United States Patent [19]
Backensfeld et al.

[11] Patent Number: 6,156,341
[45] Date of Patent: Dec. 5, 2000

[54] LOW-DOSED STEROID TABLETS THAT CONTAIN GALLIC ACID ESTER AS AN ANTIOXIDANT, PROCESS FOR PRODUCTION, AND USE

[75] Inventors: Thomas Backensfeld; Ralph Lipp; Susanne Keitel, all of Belin, Germany

[73] Assignee: Schering Aktiengesellschaft, Berlin, Germany

[21] Appl. No.: 08/765,206

[22] PCT Filed: Jun. 30, 1995

[86] PCT No.: PCT/EP95/02536

§ 371 Date: Jul. 2, 1997

§ 102(e) Date: Jul. 2, 1997

[87] PCT Pub. No.: WO96/01128

PCT Pub. Date: Jan. 18, 1996

[30] Foreign Application Priority Data

Jul. 4, 1994 [DE] Germany ............... 44 24 766
Sep. 7, 1994 [DE] Germany ............... 44 33 563

[51] Int. Cl.⁷ ............... A61K 9/20; A61K 9/28
[52] U.S. Cl. ............ 424/464; 424/465; 424/474; 514/970
[58] Field of Search .................. 424/464, 465, 424/474; 514/970

[56] References Cited

FOREIGN PATENT DOCUMENTS 1 497 836   1/1978   United Kingdom ........... A61K 31/56

*Primary Examiner*—James M. Spear
*Attorney, Agent, or Firm*—Millen White Zelano & Branigan

[57] ABSTRACT

Pharmaceutical agents that contain a gallic acid ester as an antioxidant in combination with a steroidal active ingredient, their production and their use.

10 Claims, No Drawings

LOW-DOSED STEROID TABLETS THAT CONTAIN GALLIC ACID ESTER AS AN ANTIOXIDANT, PROCESS FOR PRODUCTION, AND USE

This applications is a 371 of PCT/EP95/02536 filed Jun. 30, 1995.

The invention relates to pharmaceutical agents that contain gallic acid ester as an antioxidant in combination with a steroidal active ingredient, their production and their use.

This invention involves the production of pharmaceutical formulations that contain low-dosed steroid hormones as active ingredients and are stabilized against oxidative degradation reactions by the addition of gallic acid ester. The active ingredient concentrations in the respective form of administration, for example a tablet or coated tablet, are usually 0.1–200 µg.

Low-dosed hormones are oxidatively degraded (e.g., to the corresponding 6-hydroxy, 6-keto and delta-6 or delta-9 compounds) in pharmaceutical preparations according to what is probably a radical reaction mechanism. To prevent or delay the oxidation process in pharmaceutical preparations or to be able to guarantee the declared amount of active ingredient continuously over the storage period, antioxidants are often added. The increased stability of the steroid-containing pharmaceutical preparations that is thus achieved offers the advantage of a longer shelf life without having to use special primary packing means such as, e.g., oxyblock bags.

Antioxidants are adjuvants that are used at low concentrations to protect oxidation-sensitive substances in pharmaceutical preparations over a prolonged period or to delay their oxidation. Quite generally, they are stabilizers or oxidation inhibitors, which are used not only in pharmaceutics but also in the food, plastic, and rubber sectors. (H. Sucker, P. Fuchs, P. Speiser in Pharmazeutische Technologie [Pharmaceutical Technology], Thieme Verlag, Stuttgart, 1991; Patent WO 93/17567). In aqueous preparations the mechanism of action is known.

The mode of action of antioxidants in non-aqueous systems is presumed to involve multi-stage radical chain mechanisms in which antioxidants intervene at specific stages depending on type and as a result interrupt or inhibit the chain mechanisms (K. H. Bauer, K. H. Frömming, C. F ührer in Pharmazeutische Technologie, Thieme Verlag, Stuttgart, 1986). In non-aqueous systems, antioxidants are used mainly in semi-solid preparations such as ointments, emulsions, and suspensions (Rote Liste 1994 [Red List 1994], Editio Cantor Aulendorf). Thus, for example, contained phosphatide is protected against discoloration by adding butylhydroxytoluene and/or butylhydroxyanisole to a corticoid-containing skin preparation. Its shelf life has been extended considerably (U.S. Pat. No. 4,427,670). The use of antioxidants in different combinations increases the chemical and physical stability of an antibiotic-containing eye ointment and the corresponding eye drop (Drug. Dev. and Industrial Pharmacy 19 (1993) pp. 2595–2609).

By comparison, there are only a few solid, oral dosage forms that contain antioxidants (Stoffliste [List of Substances], 8th Edition, Werbe- u. Vertriebsgesellschaft [Advertising and Marketing Company], Eschborn). For example, i.a., DLα-tocopherol is used as an adjuvant in lynesternol- and desogestrel-containing tablet preparations. (Rote Liste 1994, Editio Cantor, Aulendorf).

In such dispersed systems, however, in addition to the selection of the suitable antioxidant, how the antioxidant is incorporated into the pharmaceutical preparation is of decisive importance for the desired improvement in stability (Walter Lund in The Pharmaceutical Codex, 12th Edition, The Pharmaceutical Press, 1994, pp. 289–292).

The object was to prevent or delay, by using antioxidants, the massive oxidative degradation of the steroidal active ingredient in the solid oral form of administration by using the lowest possible concentrations of the antioxidant, so that storage times of up to 5 years can be achieved.

Just as when the active ingredient is incorporated into the production of low-dosed tablets in the dose range of 0.1 µg to 200 µg, dilution steps at a ratio of 1:1000 to 1:100,000 are also to be implemented in incorporating the antioxidant. To ensure the required dosage accuracy per single-dosed dosage form, only pharmaceutical active ingredients with a specific grain size distribution are used (Pharm. Res. 7 (1990) pp. 962–966) and/or adjuvants with specific properties are used (EP 0 503 521 A1: Low Dose Pharmaceutical Preparations).

The object of preventing or delaying the degradation of the steroidal active ingredient and of incorporating the antioxidant as homogeneously as possible into the solid oral forms of administration is accomplished according to the teaching of the claims.

It has been found that the homogeneous dispersion of the antioxidant in the single-dosed dosage form can be achieved in that the antioxidant is dissolved in the aqueous binder solution and thus is added by spraying in suitable devices, e.g., a fluidized-bed granulator.

The advantage when using the approach according to the invention lies in the homogeneous dispersion of the antioxidant in dosage form that is achieved (Table 1). Expensive crushing of the antioxidant with the aid of micronization can be eliminated. In addition, the use of organic solvents is not necessary, which is desirable from the standpoints of safety and the environment.

In particular, it has been found that incorporating the antioxidant into the dosage form via a granular liquid offers the advantage of more efficient stabilization, i.e., to achieve a comparable improvement in stability, a lower antioxidant concentration is required than when the antioxidant is incorporated as a solid.

Suitable antioxidants are Alkyl esters of gallic acid e.g., n-propylgallate (n-propyl-3,4,5-trihydroxybenzoate) or isopropyl gallate (isopropyl-3,4,5-trihydroxybenzoate) or gallic acid methyl ester (methyl-3,4,5-trihydroxybenzoate) or gallic acid ethyl ester (ethyl-3,4,5-trihydroxybenzoate)- or gallic acid butyl ester (n-butyl-3,4,5-trihydroxybenzoate).

Steroid hormones that can be used for the production of pharmaceutical preparations according to the invention are, for example, estrogenically active steroid hormones, such as 1,3,5(10)-estratriene-3,17β-diol (estradiol), 1,9-nor-17α-pregna-1,3,5(10)-trien-20yn-3,17β-diol (ethinylestradiol), 14α,17α-ethano-1,3,5(10)-estratriene-3,17β-diol (cyclodiol) or 14α,17α-ethano-1,3,5(10)-estratriene-3,16α,17β-triol (cyclotriol); gestagenically active steroid hormones, such as 13-ethinyl-17β-hydroxy-18,19-dinor-17α-pregna-4,15-dien-20yn-3-one (gestodene) and its esters or 17β-hydroxy-1α-methyl-5α-androsten-3-one (mesterolone).

It is obvious that the preparations according to the invention can also contain mixtures of these active ingredients.

The usual concentration of the added amount of antioxidant is between 0.001% by weight and 0.1% by weight relative to the total weight of the final formulation. This concentration can increase to 5% by weight; a usual range is approximately 0.05% by weight of antioxidant, however.

The following examples are intended to explain the invention in more detail:

EXAMPLE 1

(10 μg of ethinylestradiol/tabl.: 0.01% propylgallate)

0.5455 g of ethinylestradiol, 1919.12 g of lactose, 540 g of corn starch, and 360 g of modified starch are homogeneously mixed in a fluidized-bed granulator. The powder mixture is processed into a granulate in the fluidized-bed granulator with an aqueous polyvinylpyrrolidone 25000 solution, which consists of 0.3 g of propylgallate, 150 g of polyvinylpyrrolidone 25000 and 850 g of water. After mixing in 30 g of magnesium stearate, the press dust that is obtained is pressed into tablet cores weighing 55 mg and 5 mm in diameter.

| Composition of a tablet: | |
| --- | --- |
| Ethinylestradiol | 0.0100 mg |
| propylgallate | 0.0055 mg |
| lactose | 35.1845 mg |
| corn starch | 9.9000 mg |
| modified starch | 6.6000 mg |
| polyvinylpyrrolidone 25000 | 2.7500 mg |
| magnesium stearate | 0.5500 mg |
| | 55.0000 mg |

EXAMPLE 2

(20 μg of ethinylestradiol/tabl.: 0.05% propylgallate)

6 g of ethinylestradiol, 10.542 kg of lactose, 2.97 kg of corn starch, and 1.98 g of modified corn starch are homogeneously dispersed in a mixer and transferred to a fluidized-bed granulator. The powder mixture is processed into a granulate in the fluidized-bed granulator with an aqueous solution that consists of 8.25 g of propylgallate, 825 g of polyvinylpyrrolidone 25000, and 4341 g of water, as well as 4 g of citric acid. After 165 g of magnesium stearate is mixed in, the press dust that is obtained is pressed into tablets weighing 55 mg and 5 mm in diameter.

EXAMPLE 3

(30 μg of ethinylestradiol/tabl.: 0.1% methylgallate)

1.6364 g of ethinylestradiol, 1916 g of lactose, 540 g of corn starch, and 360 g of modified starch are homogeneously mixed in a fluidized-bed granulator. The powder mixture is processed into a granulate in the fluidized-bed granulator with an aqueous polyvinylpyrrolidone 25000 solution, which consists of 3 g of methylgallate, 150 g of polyvinylpyrrolidone 25000 and 847 g of water. After 30 g of magnesium stearate is mixed in, the press dust that is obtained is pressed into tablets weighing 55 mg and 5 mm in diameter.

EXAMPLE 4

(25 μg of gestodene/tabl.: 0.01% propylgallate)

3198 g of lactose, 900 g of corn starch and 600 g of starch 1500$^{(R)}$ are processed into a homogenous powder mixture together with 1.5625 g of gestodene. In a mixer, the weighed portion of powder with 1666.5 g of a solution that consists of 0.5 g of n-propylgallate, 250 g of polyvinylpyrrolidone 25000 and 1416 g of water is processed into a granulate. After leveling, 50 g of magnesium stearate is mixed into the granulate. The material that is ready to be pressed is poured into a press and pressed into 80 mg tablets with a diameter of 6 mm.

TABLE 1

| Uniformity of the content of 0.1% propylgallate in tablets weighing 80 mg | | |
| --- | --- | --- |
| | Propylgallate incorporated as solid | Propylgallate incorporated with the binder solution |
| Average value | 93.2% | 100.4% |
| Standard deviation | 20.8% | 2.8% |
| Coefficient of variation | 22.3% | 2.8% |
| Number of tablets studied | 10 | 10 |

What is claimed is:

1. A pharmaceutical agent in solid form that contains a homogeneously dispersed gallic acid ester and a steroidal active ingredient.

2. The pharmaceutical agent according to claim 1, wherein the homogeneously dispersed gallic acid ester is provided in the agent at a concentration of 0.001–5% by weight, calculated in terms of total material.

3. The pharmaceutical agent according to claim 1 wherein the steroid active ingredient is selected from the group consisting of:

Cyclodiol,
cyclotriol,
cyproterone acetate,
estradiol undecylate,
estradiol benzoate,
estradiol valerate,
ethinylestradiol,
gestonorone caprate,
gestodene,
hydroxyprogesterone caproate,
levonorgestrel,
mesterolone,
metenolone acetate,
norethisterone,
norethinsterone acetate,
norgestrel,
prasterone enantate,
testosterone,
testosterone propionate,
testosterone anantate,
and mixtures thereof.

4. A process for production of a pharmaceutical agent according to claim 1, which comprises incorporating the homogeneous dispersion of the gallic acid ester in dosage form by dissolving the gallic acid ester in an aqueous binder solution, followed by spraying.

5. Process according to claim 4, wherein the spraying is carried out in a fluidized-bed granulator.

6. The pharmaceutical agent of claim 1, which is in tablet or coated tablet form having the steroidal active ingredient in a concentration of 0.1 to 200 μg per tablet.

7. The pharmaceutical agent of claim 1, wherein the agent is in tablet or coated tablet form.

8. The pharmaceutical agent of claim 1, wherein the gallic acid ester is an alkyl ester of gallic acid.

9. The pharmaceutical agent of claim 1, wherein the gallic acid ester is selected from the group consisting of n-propylgallate, isopropylgallate, gallic acid methyl ester, gallic acid ethyl ester and gallic acid butyl ester.

10. The pharmaceutical agent of claim 1, wherein the agent is in the form of a tablet or coated tablet, the gallic acid ester is an alkyl ester of gallic acid provided in a concentration of 0.001 to 5% by weight calculated in terms of the total material and the steroidal active ingredient is provided in a concentration of 0.1 to 200 $\mu$g per tablet.

* * * * *

UNITED STATES PATENT AND TRADEMARK OFFICE
CERTIFICATE OF CORRECTION

PATENT NO. : 6,156,341
DATED : December 5, 2000
INVENTOR(S) : Backensfeld et al.

It is certified that error appears in the above-identified patent and that said Letters Patent is hereby corrected as shown below:

Column 4,
Line 48, reads "testosterone anantate," should read -- testosterone enantate, --

Signed and Sealed this

Thirteenth Day of November, 2001

Attest:

*Nicholas P. Godici*

NICHOLAS P. GODICI
*Attesting Officer*  *Acting Director of the United States Patent and Trademark Office*